(12) United States Patent
Nieuwdorp et al.

(10) Patent No.: US 11,534,465 B2
(45) Date of Patent: Dec. 27, 2022

(54) FECAL MATTER FOR TREATMENT OF AUTOIMMUNE DISEASES

(71) Applicants: Academisch Medisch Centrum, Amsterdam (NL); Wageningen Universiteit, Wageningen (NL)

(72) Inventors: Max Nieuwdorp, Amsterdam (NL); Willem Meindert De Vos, Amsterdam (NL)

(73) Assignee: Academisch Medisch Centrum, Amsterdam (NL)

(*) Notice: Subject to any disclaimer, the term of this patent is extended or adjusted under 35 U.S.C. 154(b) by 0 days.

(21) Appl. No.: 16/976,055

(22) PCT Filed: Mar. 1, 2019

(86) PCT No.: PCT/NL2019/050130
§ 371 (c)(1),
(2) Date: Aug. 26, 2020

(87) PCT Pub. No.: WO2019/168401
PCT Pub. Date: Sep. 6, 2019

(65) Prior Publication Data
US 2021/0137994 A1    May 13, 2021

(30) Foreign Application Priority Data

Mar. 2, 2018 (NL) .................................... 2020525
Jul. 20, 2018 (NL) .................................... 2021365
Jul. 20, 2018 (NL) .................................... 2021366
Jul. 20, 2018 (NL) .................................... 2021367
Jul. 20, 2018 (NL) .................................... 2021369
Jul. 20, 2018 (NL) .................................... 2021370

(51) Int. Cl.
| | | |
|---|---|---|
| *A61K 35/37* | (2015.01) | |
| *A61P 5/38* | (2006.01) | |
| *A61P 17/06* | (2006.01) | |
| *A61P 11/06* | (2006.01) | |
| *A61P 37/06* | (2006.01) | |
| *A61P 17/00* | (2006.01) | |
| *A61P 19/02* | (2006.01) | |
| *A61P 3/10* | (2006.01) | |
| *A61P 1/00* | (2006.01) | |
| *A61P 5/14* | (2006.01) | |
| *A61K 9/00* | (2006.01) | |
| *A61K 35/74* | (2015.01) | |
| *A61K 45/06* | (2006.01) | |

(52) U.S. Cl.
CPC ............ *A61K 35/37* (2013.01); *A61K 9/0053* (2013.01); *A61K 35/74* (2013.01); *A61K 45/06* (2013.01); *A61P 1/00* (2018.01); *A61P 3/10* (2018.01); *A61P 5/14* (2018.01); *A61P 5/38* (2018.01); *A61P 11/06* (2018.01); *A61P 17/00* (2018.01); *A61P 17/06* (2018.01); *A61P 19/02* (2018.01); *A61P 37/06* (2018.01)

(58) Field of Classification Search
CPC ................................ A61K 35/74; A61P 37/00
See application file for complete search history.

(56) References Cited

U.S. PATENT DOCUMENTS

| | | | | |
|---|---|---|---|---|
| 9,433,650 | B2 * | 9/2016 | Nieuwdorp | ............... A23L 2/52 |
| 9,463,174 | B2 * | 10/2016 | Wang | ........................ G06F 8/51 |
| 9,486,487 | B2 * | 11/2016 | Cutcliffe | .............. A61K 9/0053 |
| 2014/0322213 | A1 | 10/2014 | Wang et al. | |
| 2018/0369147 | A1 * | 12/2018 | Affagard | ................ A61K 47/36 |

FOREIGN PATENT DOCUMENTS

| | | |
|---|---|---|
| FR | 3045383 A1 | 6/2017 |
| JP | 2013-537531 A | 10/2013 |
| JP | 2017-535597 A | 11/2017 |
| WO | 2016/070151 A1 | 5/2016 |
| WO | 2012/016287 A2 | 4/2022 |

OTHER PUBLICATIONS

Rossen, The Microbiome and its Therapeutic Potential in Inflammatory Bowel Diseases, University of Amsterdam, 2016. (Year: 2016).*
Mackay et al., The New England Journal of Medicine, 2001, vol. 345, No. 5, pp. 340-350 (Year: 2001).*
Timper, Diabetes Care, 36, 7, 2013 (Year: 2013).*
Shepshlovich, Lupus, 15, 2006 (Year: 2006).*
Hensvold, European Journal of Immunology, 51, 2021 (Year: 2021).*
Agace et al. "Regionalized Development and Maintenance of the Intestinal Adaptive Immune Landscape. Immunity" Apr. 18, 2017; 46(4):532-548.
De Vos "Fame and future of faecal transplantations—developing next-generation therapies with synthetic microbiomes" Microbial biotechnology (Jul. 2013) 6(4): 316-325.
Ganju et al "Microbial community profiling shows dysbiosis in the lesional skin of Vitiligo subjects" Sci Rep 6, 18761 (Jan. 2016).
Herold et al "Anti-CD3 monoclonal antibody in new-onset type 1 diabetes mellitus" N Engl J Med. vol. 346, No. 22, pp. 1692-1698 (May 2002).

(Continued)

*Primary Examiner* — Robert A Wax
*Assistant Examiner* — William Craigo
(74) *Attorney, Agent, or Firm* — TraskBritt

(57) ABSTRACT

The use of fecal matter in the treatment of a subject having autoimmune disease, wherein the fecal matter is autologous to the subject, and preferably administered to the small intestine, preferably the duodenum, of the subject. The fecal matter can be one or more constituents of autologous feces, preferably chosen from the group consisting of bacteria, viruses, bacteriophages, fungi, metabolites, microRNAs, proteins, antibodies, and/or antigens.

23 Claims, 2 Drawing Sheets

(56) References Cited

OTHER PUBLICATIONS

Kolho et al. "Fecal Microbiota in Pediatric Inflammatory Bowel Disease and Its Relation to Inflammation" Am J Gastroenterol. Jun. 2015;110(6):921-30. doi: 10.1038/ajg.2015.149. Epub May 19, 2015.

Kolmeder et al. "Comparative Metaproteomics and Diversity Analysis of Human Intestinal Microbiota Testifies for Its Temporal Stability and Expression of Core Functions" PLoS One, vol. 7, Issue 1, Jan. 2012: e29913.

Korpela et al "Intestinal microbiome is related to lifetime antibiotic use in Finnish pre-school children." Nature communications vol. 7 10410 Jan. 26, 2016, doi:10.1038/ncomms10410.

Liu et al. "The Host Shapes the Gut Microbiota via Fecal MicroRNA" Cell host & microbe vol. 19,1 (2016): 32-43. doi:10.1016/j.chom. 2015.12.005.

Manrique et al "Healthy human gut phageome" Proc Natl Acad Sci U S A.;113(37) Sep. 13, 2016; 10400-10405.

Moran et al "Interleukin-1 antagonism in type 1 diabetes of recent onset: two multicentre, randomised, double-blind, placebo-controlled trials" Lancet. (Jun. 2013) 381(9881) 26 pages.

Rajilic-Stojanovic et al. "The first 1000 cultured species of the human gastrointestinal microbiota." FEMS microbiology reviews vol. 38,5 (2014): 996-1047. doi:10.1111/1574-6976.12075.

Serna-Cock et al. "Probiotic Encapsulation" Afr J of Microbiol Res, 7(40): pp. 4743-4753 (Oct. 2013).

Tedschi et al. "Asthma and autoimmunity: a complex but intriguing relation" Expert Rev Clin Immunol. Nov. 2008;4(6):767-76.

Verdu et al. "Common ground: shared risk factors for type 1 diabetes and celiac disease" Nature Immunology, vol. 19 (Jul. 2018) pp. 685-695.

Yuan et al "Comprehensive Profiling of Fecal Metabolome of Mice by Integrated Chemical Isotope Labeling-Mass Spectrometry Analysis" 2018, 90, 5, 3512-3520, Publication Date: Feb. 6, 2018; https://doi.org/10.1021/acs.analchem.7b05355.

Holster et al., "Fecal Microbiota Transplantation in Irritable Bowel Syndrome and a Randomized Placebo-Controlled Trial", Gastroenterology, vol. 152, No. 5, (Apr. 1, 2017), XP029979290.

International Search Report for International Application No. PCT/NL2019/050130, dated Jul. 23, 2019, 5 pages.

International Written Opinion for International Application No. PCT/NL2019/050130, dated Jul. 23, 2019, 7 pages.

Kang et al., "Future prospect of faecal microbiota transpiantation as a potential therapy in asthma", Allergologia Et Immunopathologia, vol. 46, No. 3, (May 1, 2018), pp. 307-309.

Kootte et al., "Improvement of Insulin Sensitivity after Lean Donor Feces in Metabolic Syndrome Is Driven by Baseline Intestinal Microbiota Composition", Cell Metabolism, vol. 26, No. 4, (Oct. 3, 2017), pp. 611-619.

Kragsnaes et al., "Efficacy and safety of faecal microbiota transplantation in patients with psoriatic arthritis protocol for a 6-month double-blind, randomised, placebo-controlled trial", BMJ Open, vol. 8, No. 4, (Jun. 23, 2017), p. e019231.

Leszczyszyn et al., "Intestinal microbiota transpiant-current state of knowledge", Reumatologia, vol. 54, No. 1, (Jan. 1, 2016), pp. 24-28.

Yeoh et al., "The Role of the Microbiome in Rheumatic Diseases", Current Rheumatology Reports, vol. 15, No. 3, (Feb. 3, 2013), 314.

Zhao et al., Aterations of the Gut Microbiota in Hashinioto's Thyroiditis Patients, Thyroid, vol. 28, No. 2, (Feb. 1, 2018), pp. 175-186.

Japanese Notice of Reasons for Refusal for Japanese Application No. 2020-544205, dated Apr. 26, 2022, 13 pages with English translation.

Tohnyohbyoh (Diabetes mellitus), 2017, vol. 60, [1], pp. 25-29 (ENG Abstract).

* cited by examiner

FECAL MATTER FOR TREATMENT OF AUTOIMMUNE DISEASES

CROSS-REFERENCE TO RELATED APPLICATIONS

This application is a national phase entry under 35 U.S.C. § 371 of International Patent Application PCT/NL2019/050130, filed Mar. 1, 2019, designating the United States of America and published as International Patent Publication WO 2019/168401 A1 on Sep. 6, 2019, which claims the benefit under Article 8 of the Patent Cooperation Treaty to Dutch Patent Application Serial No. 2020525, filed Mar. 2, 2018, Patent Application Serial No. 2021365, filed Jul. 20, 2018, Patent Application Serial No. 2021366, filed Jul. 20, 2018, Patent Application Serial No. 2021367, filed Jul. 20, 2018, Patent Application Serial No. 2021369, filed Jul. 20, 2018 and Patent Application Serial No. 2021370, filed Jul. 20, 2018.

TECHNICAL FIELD

This disclosure relates to the prevention and/or treatment of autoimmune diseases, more specifically the use of fecal transplants in the prevention and/or treatment, preferably wherein the fecal transplants are substantially purified.

BACKGROUND

Autoimmune diseases are a class of diseases in which the immune system produces an inappropriate response against a subject's own cells, tissues and/or organs. This may result in inflammation, damage and loss of function. Common autoimmune diseases are thyroiditis, rheumatoid arthritis and Type 1 diabetes mellitus.

The causes of autoimmune diseases are not clear. However, factors such as infections and genetic disposition may play a role in triggering autoimmune diseases. Autoimmune diseases are usually diagnosed using a combination of clinical history and blood tests (detecting amongst others autoantibodies, or markers of inflammation or organ function).

Although there is a wide range of treatment options, which depend on the stage and type of autoimmune disease, there is no definitive cure for autoimmune diseases.

Treatment strategies are generally directed to relieve symptoms, minimize organ or tissue damage and preserve organ function. For example, treatment options may include replacement of organ functions (such as administering insulin in Type 1 Diabetes mellitus and thyroxine in Hashimoto's disease), non-steroidal anti-inflammatory medications (NSAIDS), corticosteroid anti-inflammatory medications (such as prednisolone), TNF α inhibitors, immunosuppressive medications, or immunoglobulin replacement therapy.

However, novel therapeutic strategies are needed to improve quality of life in patients with autoimmune diseases. There remains a need to develop a new or improved prevention and/or treatment strategy for autoimmune diseases. It is an objective of the present disclosure to meet this need.

BRIEF SUMMARY

Investigated herein is whether administration of fecal transplants, from either allogenic (healthy donor) or autologous (own) sources, have beneficial effects in patients with autoimmune disease.

Surprisingly, it has been now found that administration of autologous fecal transplants can bring about an immune reset within patients with autoimmune disease.

Without being bound by any theory, herein it is considered that the autologous fecal matter may modulate the immune system, e.g., by resetting B-cell clone function and regulatory T-cells, which in turn may inhibit autoimmune response.

It is thought that during early life, the immune system is trained via continuous crosstalk with a developing intestinal microbiome composition. In this way, the intestinal microbiome plays an essential role in modulating adaptive immune cell development, composition, and function (see e.g., Agace and McCoy Immunity 46, Apr. 18, 2017). It is this process, amongst others, that leads to a proper functioning immune system, devoid of autoimmune factors.

However, the crosstalk between the immune system and the intestinal microbiome, or the end result thereof, may be disturbed, which can lead to the production of autoimmune antibodies. The treatment according to the present disclosure may overcome this disturbance, by re-initiating the crosstalk between the immune system and the intestinal microbiome (including its specific bacteria, viruses, fungi and/or derived products such as metabolites or microbial cell envelope compounds, as well as miRNA).

Accordingly, the use of autologous fecal matter (such as autologous fecal microbiota transplants) in autoimmune diseases, may stop the autoimmune destruction of targeted tissue and re-establish immune tolerance. The present disclosure can achieve this by stimulating the immune system, wherein the autologous fecal matter is preferably administered to the duodenum (directly or indirectly such as via oral administration). The present disclosure preferably does not aim to alter the intestinal microbiome, i.e., the gut microbiota composition.

Hence, this disclosure is aimed at the treatment of autoimmune diseases, particularly endocrine autoimmune diseases (e.g., Type 1 Diabetes mellitus, Hashimoto's hypothyroidism disease, Graves's hyperthyroidism disease, and Addison's disease), Vitiligo, Celiac disease, Psoriasis (arthritis), rheumatoid arthritis, and/or Bechterew's disease. Also, prevention and/or treatment of asthma is encompassed, which may be explained by the autoimmune mechanisms, which might be operating in asthma as well (see e.g., Tedeschi and Asero Expert Rev Clin Immunol. 2008 November; 4(6):767-76).

The present disclosure also encompasses prevention of autoimmune disease. Accordingly, the autologous fecal matter of the present disclosure can be administered to a subject in order to avoid onset of autoimmune disease, for example, in subjects wherein risk markers associated with pre-stage or early stage of the respective autoimmune disease have been detected (before diagnosis of the respective autoimmune disease). Such primary or secondary prevention strategy may prevent the development of autoantibodies.

Some of the autoimmune diseases as referred herein are currently treated with immune therapy, such as by using antibodies to TNFα. However, these expensive immune therapies may only be successful in a subset of patients. This has been ascribed to deviations in the intestinal microbiota (Kolho et al. 2015 *Am J Gastroenterol.* 110(6):921-30). It is envisaged that treatment with a TNFα antagonist or anti-TNFα may be synergistic with treatment according to the disclosure, e.g., administration of autologous fecal microbiota transplant, for example, in the treatment and/or prevention of inflammatory bowel disease (IBD).

DETAILED DESCRIPTION

Figure 1:
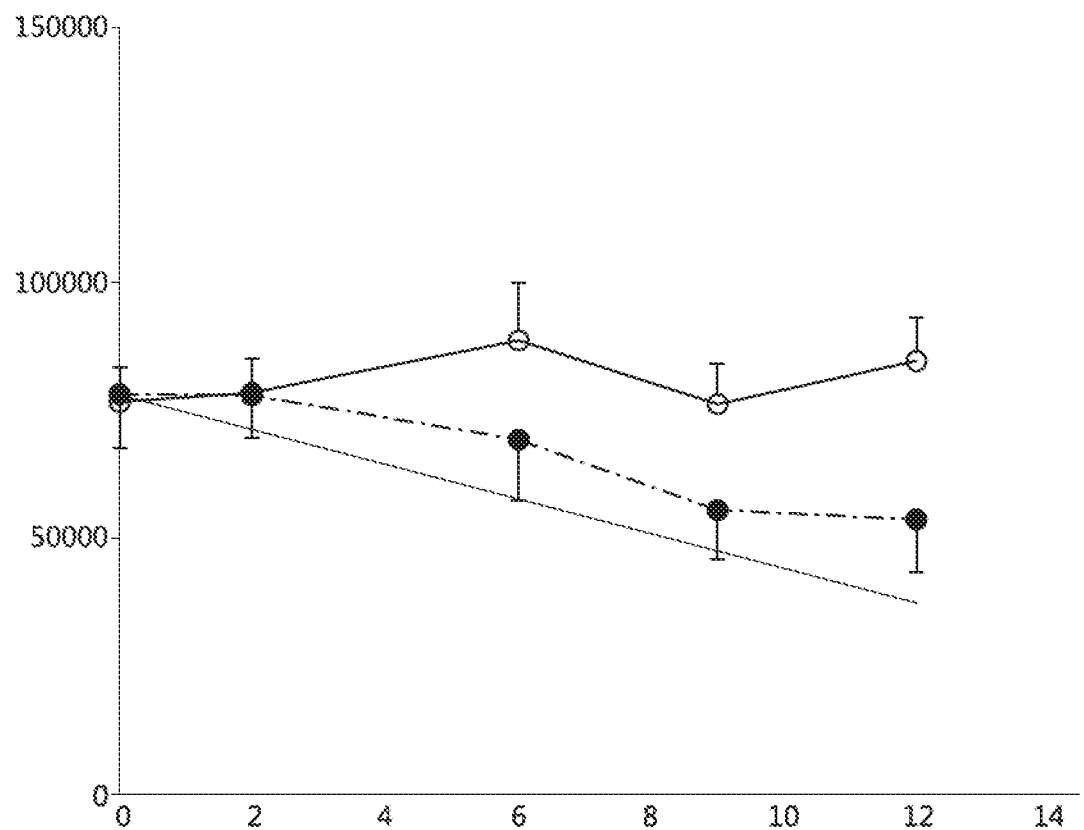
FIG. 1: Residual beta cell reserve in type 1 Diabetes patients (y-axis: AUC mixed meal test stimulated C-peptide response; x-axis: time in months). The lower, straight line represents the normal decay in residual beta cell reserve over time in diabetes mellitus type 1 (DM1) patients. The dashed line with the filled dots represents residual beta cell reserve over time in DM1 patients who received fecal material from healthy donors. The continuous line with open dots represents residual beta cell reserve over time in DM1 patients who received autologous (own) fecal material.

The disclosure relates to the use of fecal matter in the prevention and/or treatment of autoimmune disease, involving administration of the fecal matter to a subject, wherein the fecal matter is autologous to the subject. The term "autologous" as used herein denotes that the fecal matter is the subject's own fecal matter, i.e., obtained from and administrated, optionally after processing, to the same subject.

Accordingly, the disclosure provides for a method of prevention and/or treatment of a subject in need thereof, particularly a subject having an autoimmune disease such as an endocrine autoimmune disease, comprising the step of administrating fecal matter to the subject, wherein the fecal matter is autologous to the subject.

In case the fecal matter is to be employed to treat autoimmune disease, the autologous fecal matter is preferably obtained from the subject while the subject already has the autoimmune disease, i.e., while the subject has already been diagnosed as having the autoimmune disease, e.g., based on any of the diagnostic markers as referred herein. For example, the autologous fecal matter may be obtained at most 1, 2, 3, 4, 5, 6, 7, 8, 9, 10 weeks or at most 1, 2, 3, 4, 5, 6 months before treatment. In this regard, although possible, the autologous fecal matter is preferably not obtained from the subject to be treated while the subject is in healthy state (i.e., not having the autoimmune disease), nor while the autoimmune disease is in a state of remission.

Particularly, the disclosure provides for fecal matter for use in the prevention or treatment of autoimmune disease, wherein the use involves administration to a subject of fecal matter, which fecal matter is autologous to the subject, wherein the autoimmune disease is not inflammatory bowel disease (IBD), and wherein, if the use is for treatment of autoimmune disease, the fecal matter is obtained from the subject while having autoimmune disease.

The disclosure, at least a priori, preferably does not aim to alter the intestinal microbiome, i.e., the gut microbiota composition or particularly the colon microbiota composition. In fact, the microbiota composition as comprised in the autologous fecal matter of the present disclosure may be the same as the gut microbiota composition of the subject to which the autologous fecal matter is to be administered, i.e., the number of different microorganisms contained therein and/or the cell number ratios between them are roughly the same, or deviate at most 5, 3, or 1%.

In the context of this disclosure, the autoimmune disease can be any autoimmune disease, including systemic and localized (organ specific) autoimmune diseases, particularly an autoimmune disease chosen from the group consisting of endocrine autoimmune disease (e.g., Type 1 Diabetes mellitus, Hashimoto's disease, Graves's disease, or Addison's disease); skin autoimmune disease (e.g., Psoriasis or Vitiligo); rheumatoid autoimmune diseases (e.g., rheumatoid arthritis, or Bechterew's disease), and gastrointestinal autoimmune disease (e.g., Celiac disease).

Endocrine Autoimmune Diseases

Among the various autoimmune diseases, autoimmune endocrine disorders are most common. The endocrine system comprises glands that produce hormones and deliver these directly into the circulatory system, as well as feedback loops to achieve homeostasis. The organs of the endocrine system can be affected by several autoimmune diseases, characterized by different impact and severity. Sometimes multiple organs are involved, such as in polyglandular autoimmune syndrome.

Among the different autoimmune endocrine diseases, Type 1 Diabetes mellitus, Hashimoto's disease, Graves' disease, and Addison's disease are especially frequent in clinical practice.

Type 1 Diabetes Mellitus

Type 1 Diabetes mellitus is a chronic endocrine autoimmune disease wherein the pancreas produces too little or no insulin. It is generally regarded as associated with progressive beta cell destruction, and linked to an increased morbidity and mortality risk compared to healthy subjects. As beta cell function can also deteriorate in Type 2 Diabetes mellitus, the present disclosure may also concern prevention and/or treatment of Type 2 Diabetes mellitus.

It was found that fecal matter, e.g., a fecal transplant, which is autologous to the subject, can be used to prevent and/or treat Type 1 Diabetes mellitus. Such treatment may also extend the honeymoon phase in Type 1 Diabetes mellitus, i.e., the period following diagnosis wherein the pancreas is still able to produce a significant enough amount of insulin to limit exogenous insulin needs in the body and maintain blood glucose control. Extending this period can dramatically improve quality of life in patients. The treatment can also be applied to reduce severity of symptoms of Type 1 Diabetes mellitus, for example, symptoms or complications related to impaired function of eye(s), kidney(s), nerves and/or brain.

More specifically, the treatment may inhibit decay of beta cell function and/or inhibit production of autoantibodies associated with Type 1 Diabetes mellitus, such as islet (beta) cell autoantibodies, autoantibodies to insulin, autoantibodies to GAD (GAD65), autoantibodies to the tyrosine phosphatases IA-2 and IA-2β, and/or autoantibodies to zinc transporter 8 (ZnT8).

The symptoms of Type 1 Diabetes mellitus may include polyuria, polydipsia, polyphagia, weight loss, fatigue, nausea, and blurred vision. The onset of symptomatic disease can be sudden. In this regard, it is not unusual that patients with Type 1 Diabetes mellitus suffer from diabetic ketoacidosis (DKA). The following diagnostic criteria can be applied for Type 1 and Type 2 Diabetes mellitus (American Diabetes Association, ADA):

A fasting plasma glucose (FPG) level ≥126 mg/dL (7.0 mmol/L), or

A 2-hour plasma glucose level ≥200 mg/dL (11.1 mmol/L) during a 75-g oral glucose tolerance test (OGTT), or A random plasma glucose ≥200 mg/dL (11.1 mmol/L) in a patient with classic symptoms of hyperglycemia or hyperglycemic crisis.

Additionally and/or alternatively, C-peptide response after a mixed meal test can be assessed, as described in the Example and/or as described by Lachin et al (2011 PLoS ONE Vol. 6(11) e26471).

Type 1 Diabetes mellitus and/or its preceding symptoms can be confirmed by the presence of one or more autoimmune markers, which include islet (beta) cell autoantibodies, autoantibodies to insulin, autoantibodies to GAD (GAD65), autoantibodies to the tyrosine phosphatases IA-2 and IA-2(3, and autoantibodies to zinc transporter 8 (ZnT8) as well as increased HbA1c and altered glucose tolerance.

Hashimoto's Disease

Hashimoto's disease is an organ specific autoimmune disorder with the highest occurrence. It is also referred to as Hashimoto's thyroiditis, or chronic lymphocytic thyroiditis and is regarded as an autoimmune disease in which the thyroid gland is gradually destroyed. The causes of Hashimoto's disease are still unclear, although an inappropriate cell-mediated immune response and autoantibody production against the thyroid gland are generally thought to be involved.

Until thyroid hypofunction becomes apparent, an enlargement of the thyroid is typically the only symptom. However, the disease can progress into hypothyroidism, thereby often leading to symptoms including edema, weight gain, and fatigability (susceptible to fatigue), sensitivity to cold and diarrhea, and physical findings such as dry skin, hoarseness, bradycardia, and/or a prolonged relaxation phase of the Achilles tendon reflex.

Hashimoto's disease may be confirmed by the presence of anti-thyroid peroxidase (TPO) antibodies and anti-thyroglobulin (Tg) antibodies in the patient's serum. Further, an elevated level of thyroid-stimulating hormone (TSH), and lowered levels of free T4 (FT4), lowered levels of free T3, and/or elevated levels of anti-microsomal antibodies, in comparison to the average in healthy individuals, can help obtain positive diagnosis.

Hashimoto's disease is currently treated with thyroid hormone replacement agents such as levothyroxine (FT4 supplementation), triiodothyronine (T3 supplementation) or desiccated thyroid extract. The present inventors found that fecal matter according to the present disclosure, e.g., a fecal microbiota transplant, which is autologous to the subject, can be used to prevent and/or treat Hashimoto's disease, optionally in combination with thyroid hormone replacement agents as described above. The treatment according to the present disclosure can also be applied to reduce severity of symptoms of Hashimoto's disease, for example, one or more symptoms or complications as described above.

Graves' Disease

Graves' disease is an autoimmune disease that affects the thyroid, and is the most common cause of hyperthyroidism. The disease can be characterized by the presence of autoantibodies in the serum that bind the thyrotropin receptor, i.e., the thyroid stimulating hormone (TSH) receptor. These anti-TSH receptor antibodies (TBII) overstimulate the thyroid gland, which may lead to goiter and signs of thyrotoxicosis as well as involvement of the eye muscles in a subset of patients (Graves ophthalmopathy).

Among the symptoms are hyperthyroidism, goiter, and orbitopathy. Other major symptoms include weight loss (with increased appetite), fatigability, shortness of breath, hyperhidrosis, finger tremors, diarrhea, periodic paralysis (in male), and muscle weakness. With regard to Graves ophthalmopathy, patients may suffer from proptosis of the eyes, blurred vision and dry/red eyes (in rare cases it can lead to blindness). Two signs are truly specific of Graves' disease and not seen in other hyperthyroid conditions: exophthalmos and pretibial myxedema.

Graves' disease may be confirmed by low serum TSH level (sometimes not detectable) and/or elevations in free T3 and free T4, in comparison to health individuals. Patients may typically be positive for anti-TSH receptor antibodies (TBII) in their serum.

Current treatment of Graves' disease may involve administration of anti-thyroid drugs (block and replacement therapy), radioiodine (radioactive iodine 1-131); and/or thyroidectomy (surgical excision of the gland). Usually, strumazol and methimazole (PTU) are prescribed followed by thyroid hormone replacement agents such as levothyroxine (FT4 supplementation), triiodothyronine (T3 supplementation) or desiccated thyroid extract.

Alternatively or in combination with the above-described treatment, it has been found that fecal matter according to the disclosure, e.g., a fecal microbiota transplant, which is autologous to the subject, can be used to prevent and/or treat Graves' disease including ophthalmopathy. The treatment according to this disclosure can also be applied to reduce severity of symptoms of Graves' disease, for example, one or more symptoms or complications as described above.

Addison's Disease

Addison's disease is a chronic endocrine autoimmune disorder in which the adrenal glands do not produce sufficient steroid hormones. The disease is caused by destruction of the adrenal glands (both cortex and medulla produced hormones). The disease may be a manifestation of polyglandular autoimmune syndrome involving complications by other organ-specific autoimmune disorders (e.g., Type 1 Diabetes mellitus, Hashimoto's disease, Vitiligo).

Hyperpigmentation due to increased secretion of ACTH is a characteristic clinical sign of Graves' disease. Other symptoms include abdominal pain in the stomach region, orthostasis and weight loss.

Medical examination will typically determine if orthostasis, hypoglycemia, hyponatremia, hyperkalemia, and peripheral blood eosinophilia are present. To confirm Addison's disease, demonstration of low adrenal hormone levels even after stimulation (called the ACTH stimulation test or synacthen test) with synthetic pituitary ACTH hormone tetracosactide is generally performed for the diagnosis.

Treatment generally involves replacement therapy with oral hydrocortisone and/or mineralocorticoids like fludrocortisone (if the adrenal medulla is also involved). The present inventors found that fecal matter according to the present disclosure, e.g., a fecal microbiota transplant, which is autologous to the subject, can be used to prevent and/or treat Addison's disease, optionally in addition to treatment with hydrocortisone. The treatment according to the present disclosure can also be applied to reduce severity of symptoms of Addison's disease, for example, one or more symptoms or complications as described above.

Skin Autoimmune Disease

Psoriasis (Arthritis)

Psoriasis is a chronic autoimmune disease that leads to rapid production of skin cells. The underlying etiology is that T cells attack healthy skin cells, which causes the skin cell production process to go into overdrive. The new cells are pushed to the skin's surface, where they pile up. This results in the plaques and red inflamed areas of skin, which are most commonly associated with psoriasis. Subtypes of psoriasis include (1) plaque psoriasis, which is the most frequently occurring type of psoriasis. It is characterized by red, inflamed patches that cover areas of the skin, typically on the elbows, knees, and scalp. These patches are often covered with whitish-silver scales or plaques;

(2) Guttate psoriasis, which is the form of psoriasis that is common in children and causes small pink spots, typically on the torso, arms, and legs;

(3) Pustular psoriasis, which is more common form of psoriasis in adults and causes white, pus-filled blisters and areas of red inflamed skin, typically on the hands or feet;

(4) Inverse psoriasis, which causes bright areas of red, shiny, inflamed skin. Patches of inverse psoriasis typically develop under armpits or breasts, in the groin, or around skinfolds;

(5) Erythrodermic psoriasis, which is a severe and rare type of psoriasis. This form often covers large sections of the body where the skin may appear sunburned. A person with this type of psoriasis may run a fever or become very ill, and this form of psoriasis can be life-threatening;

(6) Psoriatic arthritis with involvement of the joints.

Psoriasis symptoms are different among patients. Common symptoms include red patches of skin covered with thick, silvery scales, small scaling spots (commonly seen in children), dry, cracked skin that may bleed, itching, burning or soreness, thickened, pitted or ridged nails, and/or swollen and stiff joints. Most types of psoriasis can go through cycles, flaring for a few weeks or even months, then subsiding for a period or even going into remission. Psoriasis arthritis (or psoriatic arthritis) is a condition wherein swollen, sore joints of arthritis occur together with psoriasis.

For mild disease that involves only small areas of the body, topical treatments (applied on the skin), such as creams, lotions, and sprays, are generally prescribed. Occasionally, a local injection of steroids directly into a tough or resistant isolated psoriatic plaque may be helpful.

Tumor necrosis factor (TNF) antagonists (or anti TNFα therapy) have become first-line agents in the treatment of moderate-to-severe psoriasis or psoriatic arthritis. Examples include infliximab, etanercept, and adalimumab. Anti TNFα therapy has been found effective in treating both psoriasis and psoriatic arthritis and may also reduce the risk of cardiovascular events. The present inventors found that, in addition or alternatively, fecal matter according to the present disclosure, e.g., a fecal microbiota transplant, which is autologous to the subject, can be used to prevent and/or treat psoriasis and/or psoriatic arthritis. In addition, the treatment according to the present disclosure can also be applied to reduce severity of symptoms of psoriasis and psoriatic arthritis, for example, one or more symptoms or complications as described above. Particularly the combined treatment with a TNF antagonist or anti-TNFα and treatment according to the present disclosure may be synergistic.

Vitiligo

Vitiligo is a disease wherein white patches of skin appear on different parts of the body. It is generally thought that this is due to autoimmune processes that destroy the cells that make pigment (color) in the skin, i.e., melanocytes. Vitiligo can also occur in mucous membranes (such as inside the mouth and nose) and in the eye.

Recent studies reveal dysbiosis in the diversity of microbial community structure in the skin microbiome of vitiligo subjects. Although the individual specific microbiome signature is dominant over the vitiligo-specific microbiota, a clear decrease in taxonomic richness and evenness can be noted in lesional patches (Ganju et al Sci Rep. 2016 Jan. 13; 6:18761).

The white patches of vitiligo are more common in areas where the skin is exposed regularly to sunlight. The patches may be on the hands, feet, arms, face, and lips, but occasionally also on the armpits and groin, around the mouth, eyes, nostrils, navel, genitals, rectal areas. Further, people with vitiligo often have hair that turns gray early (e.g., before age 35).

Ultraviolet (UV) light can be used particularly in the early phase of vitiligo for diagnosis and to determine the effectiveness of UV treatment. Skin with vitiligo, when exposed to UV, typically will glow blue. In contrast, healthy skin will show no reaction.

Vitiligo can be classified into segmental vitiligo (SV) and non-segmental vitiligo (NSV), where NSV is the most common type of vitiligo.

In non-segmental vitiligo (NSV), there typically is symmetry in the location of the patches of depigmentation. In extreme cases, little pigmented skin remains, which is referred to as vitiligo universalis. NSV can initiate at any age, whereas segmental vitiligo is far more prevalent in teenage years.

Segmental vitiligo (SV) tends to affect areas of skin that are associated with dorsal roots from the spinal cord and is most often unilateral. It is much more stable/static in course. SV typically does not improve with UV light therapy, but surgical treatments such as cellular grafting can be effective.

There is no definitive cure for vitiligo but several treatment options are available, including ultraviolet light and/or creams. Topical preparations (i.e., creams) of immune suppressing medications including corticosteroids or glucocorticoids (such as clobetasol and/or betamethasone) and calcineurin inhibitors (such as tacrolimus and/or pimecrolimus) are considered to be first-line vitiligo treatments, while UV(B) therapy is considered a second-line treatment for vitiligo.

The present inventors found that, in addition or alternatively to the above-described treatment(s), fecal matter according to the present disclosure, e.g., a fecal microbiota transplant, which is autologous to the subject, can be used to prevent and/or treat vitiligo. Further, the treatment according to the present disclosure can also be applied to reduce severity of symptoms of vitiligo, for example, one or more symptoms or complications as described above.

Rheumatoid Disorder

Rheumatoid Arthritis

Rheumatoid arthritis (RA) can be seen as an autoimmune disease in which the immune system attacks the joints. This leads to inflammation that causes the tissue that lines the inside of joints (the synovium) to thicken, resulting in painful joints.

If not treated, RA can damage cartilage, the elastic tissue that covers the ends of bones in a joint, and even the bones themselves. Eventually, there can be loss of cartilage, joints can become loose, unstable, painful and lose their mobility, or even deform. Unfortunately, joint damage generally cannot be reversed, and therefore early diagnosis and treatment is recommended to control RA.

RA most commonly occurs in the joints of the hands, feet, wrists, elbows, knees and ankles. RA can also affect body systems, such as the cardiovascular or respiratory systems, and is then called systemic RA. In the early stages, people with RA may experience tenderness and pain in the joints.

Symptoms of RA include stiffness and joint pain, specifically small joints (wrists, certain joints of the hands and feet), and typically for six weeks or longer. Along with pain, many people experience fatigue, loss of appetite and a mild fever.

No single test can definitely confirm RA, but blood tests can be performed that measure inflammation levels and look for biomarkers such as antibodies that are linked with RA.

A high erythrocyte sedimentation rate and a high C-reactive protein (CRP) level, in comparison to healthy individuals, are biomarkers of inflammation. A high ESR or high CRP is not specific to RA, but when combined with the presence of RA-related antibodies, can confirm RA diagnosis.

Rheumatoid factor (RF) is an antibody found in the majority of people with RA. Because RF can occur in other inflammatory diseases, it is not a definitive sign of having RA. However, a different antibody—anti-cyclic citrullinated peptide (anti-CCP)—occurs primarily in RA patients. That makes a positive anti-CCP test a stronger indication of RA. In addition, an X-ray, ultrasound or magnetic resonance imaging scan can be performed to look for joint damage, such as erosions and narrowing of joint space.

With respect to treatment, nonsteroidal anti-inflammatory drugs (NSAIDs) are generally prescribed, which can ease arthritis pain and inflammation. Examples of NSAIDs include ibuprofen, ketoprofen and naproxen sodium. Further, corticosteroids, including prednisone, prednisolone and methyprednisolone, can be administered as anti-inflammatory medications.

DMARDs, i.e., disease-modifying antirheumatic drugs, may be used to slow down the progression of the disease. DMARDs include methotrexate, hydroxycholorquine, sulfasalazine, leflunomide, cyclophosphamide and azathioprine. A subcategory of DMARDs is known as "JAK inhibitors," which block the Janus kinase, or JAK, pathways. An example is Tofacitinib.

Biologicals may work more quickly than traditional DMARDs, and are injected or given by infusion. In many people with RA, a biological can slow, modify or stop the disease. Particularly preferred are tumor necrosis factor (TNF) antagonists (anti TNFα therapy).

It has been found that, in addition or alternatively to the above-described treatment(s), fecal matter according to the present disclosure, e.g., a fecal microbiota transplant, which is autologous to the subject, can be used to prevent and/or treat Rheumatoid arthritis and/or one or more of its symptoms as described above. The combined treatment according to the present disclosure (e.g., with fecal microbiota transplant) with a TNF antagonist or anti-TNFα may be synergistic.

Bechterew's Disease

Bechterew's disease (or Ankylosing Spondylitis) is a chronic autoimmune rheumatoid disorder involving particularly the axial skeleton. Typically, it presents in male adults of 20-30 years of age.

The most serious symptoms are neck and lower back pain. A typical symptom is nocturnal pain, as well as inflammation of the sacroiliac joint. In a some patients, bony deformities of the spine can occur, which may result in motion restriction. Apart from these spinal complaints, inflammation of peripheral joints is common.

In order to diagnose Bechterew's disease, examination of the vertebral column is performed to assess restrictions in cervical and lumbar spine mobility. A Schober test can be helpful in estimating the amount of lumbar forward flexion restriction. The diagnosis could be confirmed by discovery of HLA-B27 antigens in patient's blood.

Treatment options include administration of NSAID, sulfasalazine, methotrexate, leflunomide, corticosteroid, TNFα inhibitor(s). The present inventors found that, in addition or alternatively to the above-described treatment(s), fecal matter according to the present disclosure, e.g., a fecal microbiota transplant, which is autologous to the subject, can be used to prevent and/or treat Bechterew's disease and/or one or more of its symptoms as described above. Particularly the combination of treatment according to the present disclosure (e.g., with fecal microbiota transplant) with a TNF antagonist or anti-TNFα may be synergistic.

Gastrointestinal Autoimmune Disease

Celiac Disease

Celiac disease (or coeliac disease) is an autoimmune disorder where the ingestion of gluten leads to damage of the small intestinal epithelial cells. It may typically occur in genetically predisposed people and in combination with type 1 diabetes. Celiac disease and Type 1 Diabetes mellitus may have similar pathogenesis wherein heritable genetic factors as well as dietary and microbial exposures may play a role, particularly in early life (see e.g., Verdu and Danska *Nature Immunology*|VOL 19|JULY 2018|685-695).

When people with celiac disease eat gluten (a protein found in wheat, rye and barley), their body initiates an immune response that attacks the small intestine, leading to damage of the villi (small fingerlike projections that line the small intestine). When the villi get damaged, nutrients cannot be absorbed properly by the intestine. Symptoms are abdominal cramps, malnutrition and osteoporosis.

There are several serologic (blood) tests available that screen for celiac disease antibodies, but the most commonly used is a tTG-IgA test. For this test to work, the patient must be consuming gluten. In addition, diagnosis for Celiac disease can be reached by an endoscopic biopsy. A biopsy is then taken of the small intestine, which can subsequently be analyzed to see if there is any damage consistent with celiac disease. The diagnosis may be confirmed when improvement is seen while on a gluten-free diet.

Currently, the only treatment for celiac disease is a strict gluten-free diet. People living gluten-free must avoid foods with wheat, rye and barley, for example, bread and beer. Ingesting small amounts of gluten can trigger small intestine damage. The present inventors found that, in addition or alternatively to the above-described treatment(s), fecal matter according to the present disclosure, e.g., a fecal microbiota transplant, which is autologous to the subject, can be used to prevent and/or treat Celiac disease and/or one or more of its symptoms as described above.

Asthma

In the context of the present disclosure, also the prevention and/or treatment of asthma is foreseen, in view of autoimmune mechanisms that might be operating in asthma as well.

Asthma is a common chronic inflammatory disease of the airways of the lungs. It can be characterized by reversible airflow obstruction and bronchospasm. Symptoms include episodes of coughing, wheezing, chest tightness, and shortness of breath.

There is currently no definitive diagnostic test for asthma, and diagnosis is typically based on the pattern of symptoms and response to therapy over time. A diagnosis of asthma can be made if there is a history of recurrent wheezing, coughing or difficulty breathing and these symptoms occur or worsen due to exercise, viral infections, allergens and/or air pollution; also FEV1 test upon bronchodilators are done to study effect on lung function.

An effective treatment for asthma is identifying what triggers the disease, such as cigarette smoke, pets, or aspirin, and eliminating exposure to these triggers. In addition, bronchodilators are often recommended. In the case of mild but persistent disease, low-dose inhaled corticosteroids or alternatively, leukotriene antagonists or mast cell stabilizers can be applied. For serious asthma, i.e., patients who have daily attacks, inhaled corticosteroids, i.e., in a higher dose, can be used.

The present inventors found that, in addition or alternatively to the above-described treatment(s), fecal matter according to the present disclosure, e.g., a fecal microbiota transplant, which is autologous to the subject, can be used to prevent and/or treat asthma and/or one or more of its symptoms as described above.

The effectiveness of the treatment according to the present disclosure confirms a link between intestinal microbiome composition and risk of developing asthma, which has been postulated by Korpela et al (*Nat Commun.* 2016 Jan. 26; 7:10410).

Other Conditions

The present disclosure may also be used in the context of preventing and/or treating other autoimmune diseases, particularly including autoimmune hepatitis, Diabetes mellitus Type 1a and/or 1b, polyglandular autoimmune syndrome, Guillain-Barre syndrome, Multiple sclerosis, Myasthenia gravis, Pernicious anemia, Primary biliary cirrhosis, Sclerosing cholangitis, Antiphospholipid antibody syndromes, Dermatomyositis, Mixed connective tissue disease, Polymyalgia rheumatica, Polymyositis, Scleroderma, Sjögren's syndrome, and Systemic Lupus Erythematosus. However, it is also envisaged that any of the above mentioned diseases is excluded from the present disclosure.

Additionally, the fecal matter according to the present disclosure may be used to prevent and/or treat an allergy, also known as allergic diseases, which are conditions caused by hypersensitivity of the immune system to typically harmless substances in the environment. Common allergies include hay fever (plant pollen allergy) and food allergy (relating e.g., to cow's milk, soy, eggs, wheat, peanuts, tree nuts, fish, and/or shellfish).

The present disclosure may also allow for the prevention and/or treatment of the following diseases, but preferably these diseases are excluded from the scope of the present disclosure: gastrointestinal disorders, *Clostridium difficile* infection, Morbus Crohn (Crohn's disease), Colitis Ulcerosa or Inflammatory Bowel Disease (IBD), and/or Irritable bowel syndrome (IBS). Alternatively and/or additionally, any of the following diseases may be excluded from the present disclosure: systemic and localized (organ specific) autoimmune diseases, endocrine autoimmune disease, Type 1 Diabetes mellitus, Type 2 Diabetes mellitus, Hashimoto's disease, Graves's disease, or Addison's disease, skin autoimmune disease, Psoriasis or Vitiligo, rheumatoid autoimmune diseases, rheumatoid arthritis, Bechterew's disease, and gastrointestinal autoimmune disease, Celiac disease.

Treatment According to the Present Disclosure

In a preferred embodiment, the fecal matter according to the present disclosure is administered to the gastrointestinal tract of the subject, preferably the small intestine, most preferably the duodenum, of the subject. The duodenum is the first section of the small intestine in most higher vertebrates, including mammals. The duodenum precedes the jejunum and ileum and is the shortest part of the small intestine. In humans, the duodenum is a hollow tube of 25-38 cm, which connects the stomach to the distal duodenum. It begins with the duodenal bulb and ends at the suspensory muscle of duodenum.

Although it is also possible to administer the fecal matter to the colon (or cecum) of the subject, administration to the colon (or cecum) of the subject is preferably not encompassed by the present disclosure.

As will be clear, the fecal matter according to the present disclosure can be feces, i.e., excreta discharged from the intestine (anus), such as (morning) stool, or part thereof and/or a composition derived therefrom.

Additionally and/or alternatively, the fecal matter according to the present disclosure may refer to one or more constituents/fractions of autologous or allogenic feces, wherein the constituents/fractions are preferably chosen from the group consisting of bacteria, viruses, bacteriophages, fungi, metabolites, proteins, and/or microRNAs (e.g., as disclosed in Lui, Cell Host Microbe. 2016 Jan. 13; 19(1):32-43), antibodies, antigens, immune modulating/signaling components, entero(endocrine) signaling components, neural signaling components and/or structural components. The term "signaling" as used herein thus denotes that the component is able to trigger or induce a cell, in particular, a (entero-endocrine or neural) cell of the subject as disclosed herein, to act differently, such as excreting certain compounds or presenting a change in the transcriptome or gene expression. For example, entero-endocrine signaling components can trigger entero-endocrine cells to release functional molecules. Constituents of the microbiome such as viruses, bacteria, fungi etc and/or derived products such as metabolites or bacterial capsule compounds including miRNA) may modulate the immune system—by resetting B cell clone function and regulatory T-cells, which in turn may inhibit autoimmune response.

The constituents/fraction may, for example, be or one or more of the constituents as disclosed by de Vos (*Microb Biotechnol.* 2013 July; 6(4): 316-325). The specific one or more constituents/fractions as obtainable from autologous source, which have the desired therapeutic or preventive effect may also be obtained from allogenic source. Such one or more constituents/fractions as obtainable from allogenic source and having the desired therapeutic and/or preventive effect are therefore explicitly encompassed by the present disclosure.

The fecal matter according to the present disclosure and obtained from autologous or allogenic source may thus be or comprise bacteria, i.e., microbiota or intestinal microbial cells, wherein the phylum may be one (or a combination) chosen from the group consisting of:

Firmicutes, such as belonging to the genera *Eubacterium, Intestinimonas, Faecalibacterium, Christensenella, Anaerostipes, Agathobacter, Roseburia, Coprococcus, Clostridium, Subdoligranulum, Anaerotruncus, Flavinobacter, Ruminococcus, Butyricicoccus, Butyrovibrio, Sporobacter, Papilibacter, Oscillobacter, Oscillospora, Veilonella, Lactobacillus, Streptococcus;*

Proteobacteria such as belonging to the genera *Escherichia* or *Enterobacter;*

Actinobacteria such as belonging to the genera *Bifidobacterium* or *Colinsella*;
Bacteroidetes such as belonging to the genera *Bacteroides, Prevotella* or *Alistipes*; and/or
Verrucomicrobia such as belonging to the genus *Akkermansia*.

The fecal matter may also be or comprise microbiota or intestinal microbial cells chosen from Eukarya, Archaea, and Bacteria, preferably chosen from the group of 1057 species as disclosed by Rajilić-Stojanović and de Vos (2014 *FEMS Microbiol Rev.* 38(5):996-1047).

A total of between $10^4$ and $10^{16}$, $10^4$ and $10^{15}$, 104 and $10^{14}$, $10^6$ and $10^{12}$, preferably between $10^8$ and $10^{10}$, bacterial cells may preferably be comprised in the fecal matter.

The present disclosure also encompasses that the fecal matter according to the present disclosure (autologous or allogenic) concerns or comprises one or more viruses, such as chosen from the group consisting of adenovirus, rotavirus, sapovirus, enterovirus, and/or reovirus. At the same time or as an alternative, the fecal matter concerns or comprises one or more bacteriophages such as isometric bacteriophages and/or tailed bacteriophages (caudovirales). For example, the bacteriophages can be one or more of the 23 shared bacteriophages or on or more of the 44 bacteriophage groups as disclosed by Manrique et al (2016 *Proc Natl Acad Sci US A.* 2016 13; 113(37):10400-5).

Additionally and/or alternatively, the fecal matter according to the disclosure (autologous or allogenic) may be or comprise one or more fungi and/or yeasts, preferably chosen from the group consisting of *Candida* yeasts and yeasts of the family Dipodascaceae (*Galactomyces, Geotrichum, Saprochaete*), *Malassezia* and the filamentous fungus *Cladosporium, Penicillium* and *Debaryomyces* species, *Saccharomyces cerevisiae*, and/or *Aspergillus* species.

It is also foreseen that the fecal matter according to the disclosure (autologous or allogenic) is or comprises metabolites, i.e., compounds and/or substances formed in (human and/or microbiota) metabolism, for example, one or more of the 2302 (potential) metabolites, the 1388 positively identified metabolites and/or the 308 confirmed metabolites as disclosed by Bi-Feng Yuan et al (2018 Anal. Chem., Article ASAP DOI: 10.1021/acs.analchem.7b05355), including metabolites with carboxyl, carbonyl, amine, and/or thiol functional moieties.

Preferably the metabolite(s) are one or more chosen from short chain fatty acids (SCFA), free fatty acids (FFA), branched chain amino acids (BCAA), polyunsaturated fatty acids (PUFA), bile acids, phenyllactic acids (PLA), lipoteichoic acids (LTA) and/or chosen from the group consisting of p-hydroxyphenylacetic acid, taurocholic acid, butyric acid, acetic acid, pipecolic acid, ethanol, gamma-aminobutyric acid, glycolic acid, homovanillic acid, fumaric acid, glycocholic acid, d-galactose, glutamic acid, l-tyrosine, l-phenylalanine, l-alanine, l-proline, l-threonine, l-tryptophane, d-mannose, l-isoleucine, l-histidine, l-lysine, l-lactic acid, oleic acid, phenylacetic acid, palmitic acid, phenol, propionic acid, pyruvic acid, succinic acid, d-ribose, uridine, 3-hydroxybutyric acid, 3-(3-hydroxyphenyl)propanoic acid, 3,4-dihydroxyhydrocinnamic acid, 3-hydroxyphenylacetic acid, adipic acid, butanone, vanillic acid, and/or 4-hydroxybenzoic acid, and/or bile acids chosen from the group consisting of cholic acid, glycocholic acid, taurocholic acid, deoxycholic acid, chenodeoxycholic acid, glycochenodeoxycholic acid, taurochenodeoxycholic acid, lithocholic acid.

However, it is particularly preferred that the fecal matter according to the present disclosure (autologous or allogenic) is or comprises proteins, i.e., a protein fraction of autologous feces. In this regard, the term "protein" refers to molecules consisting of or comprising a chain of amino acids, without reference to a specific mode of action, size, 3 dimensional structure or origin. Preferably, this concerns proteins with a molecular weight of between 1,000 and 500,000 dalton, or between 1,000 and 100,000 dalton or 100,000 and 500,000 dalton, or between 100,000 and 300,000 dalton. The proteins may be degradation products from the intestine, bacterial proteins and/or dietary proteins. Proteins can be extracted from fecal samples e.g., by bead beating (see e.g., Kolmeder et al. 2012 PLoS One. 7: e29913). These proteins may vary in size, being antibodies, peptides, and/or enzymes, and thus may have enzymatic activity such as alkaline phosphatase.

The proteins can be one or more proteins as disclosed in Kolmeder et al (2012 PLoS One. 7: e29913). In a specific embodiment, the proteins are antibodies, for example, immunoglobulin A (IgA), immunoglobulin E (IgE); immunoglobulin M (IgM) and/or immunoglobulin G (IgG).

It is also foreseen that the fecal matter according to the disclosure (autologous or allogenic) is or comprises antigen(s), i.e., a substance or molecule capable of inducing an immune response and/or immune tolerance induction in the subject, which in turn may lead to the inhibition of an autoimmune reaction.

As mentioned herein before, the fecal matter according to the disclosure (autologous or allogenic) may be or comprise (structural) components, e.g., components that communicate and/or interact with the recipient's immune system, i.e., immune system communication molecules, which may, for example, be derived from microbiota.

In a preferred embodiment, such components are one or more Toll-like receptor ligands. It has been speculated that Toll-like receptor (TLR) activation might participate in autoimmune disease. In the present disclosure, such one or more Toll-like receptor ligand may be chosen from the group consisting of ligands for TLR1, TLR2, TLR3, TLR4, TLR5, TLR6, TLR7, TLR8, TLR9, TLR10, TLR11, TLR12, TLR13, TLR14 and/or from bacterial lipoprotein and/or peptidoglycans, bacterial peptidoglycans, double-stranded RNA, lipopolysaccharides, bacterial flagella, bacterial lipoprotein, single-stranded RNA (bacterial and/or viral), single-stranded RNA (bacterial and/or viral), phagocytized bacterial RNA, CpG DNA, profilin from *Toxoplasma gondii*, also possibly uropathogenic bacteria, profilin from *Toxoplasma gondii*, and/or bacterial ribosomal RNA or mannose binding lectin (MBL).

The prevention and/or treatment according to the disclosure may involve administering the fecal matter, which has been obtained or derived from the subject, to the small intestine, preferably the duodenum, of the subject. In this regard, the fecal matter may be administered by enteral, preferably by oral, nasal or rectal administration, and/or by duodenal administration such as by means of a (naso) duodenal tube. Although foreseen, but preferably excluded, is intravenous administration.

The fecal matter may be applied in an effective amount, i.e., a quantity sufficient to achieve a desired therapeutic and/or prophylactic effect, e.g., an amount that results in the treatment and/or prevention of the respective condition, for example, at least 0.1, 0.5, 1, 10, 50, 100, 500 mg or at least 1, 5, 10, 25, 50, 100, 250, 500 g. In the context of therapeutic or prophylactic applications, the amount to be administered to the subject may depend on the type and severity of the disease or condition and on the characteristics of the subject, such as general health, age, sex, body weight and tolerance to drugs. It may also depend on the degree, severity and type of disease or condition. The skilled artisan will be able to determine appropriate dosages depending on these and other factors.

In a preferred embodiment, the prevention and/or treatment according to the disclosure involves at least 1, 2, 3, 4, 5, 6, 7, 8, 9, 10, 20, 30, 40, 50 separate administrations of fecal matter obtained from the subject to the small intestine, preferably the duodenum of the subject, preferably with intervals of at least 1, 2, 3, 4, 5, 6, 7, 8, 10, 20, 30, 40, 50 weeks between the separate administrations. The prevention and/or treatment may also involve daily, weekly, monthly administrations, such as once or twice within every 1, 2, 3, 4, 5, 6, 7, 8, 9, 10 days/weeks/months and/or may be during a period of at least 1, 2, 3, 4, 5, 6, 7, 8, 9, 10, 20, 30, 40, 50 weeks (or months or even years).

The fecal matter may be comprised in liquid medium and/or preferably does not comprise solids having a diameter of more than 1, 2, 3, 4, 5, 10, 15, 20, 25, 50, 75, 100, 200, 400, 600, 800, or 1000µ, preferably obtained by mixing autologous feces with aqueous medium (e.g., aqueous solution with 0.5-1.5 wt. % NaCl, e.g., 0.9 wt % NaCl) and subsequent filtering (though a filter with pores of at most 500, 400, 300, 200, 100, 50, 40, 30, 20, 10 µm) and/or centrifugation (e.g., with at least 5,000, 10,000 g for at least 1, 2, 3, 4, 5, 10 min). Such composition may be referred to as an extract. With the term "solids" is means discrete particles with at most 30, 20, 10, 5, 1 wt. % water.

It is also foreseen that the fecal matter is (substantially) purified or enriched relative to collected feces, e.g., the concentration of one or more (groups of) constituents of the feces is increased relative to the feces and/or the concentration of one or more (groups of) constituents in the fecal matter is at least 40, 50, 60, 70, 80, 90, 95, 99 wt. % relative to the total of constituents and/or relative to the total fecal matter. Such processed fecal matter can, for example, be obtained by:

- centrifugation and/or filtration as discussed above e.g., to separate solids from liquid fraction;
- filtration of fecal matter (e.g., in liquid medium) into differently sized components;
- disintegration of the fecal matter, for example, by bead beating, that disrupts microbial cells but keeps proteins largely intact;
- lyophilisation of the fecal matter, as described herein elsewhere; and/or
- sonication, e.g., to free desired components from surrounding structures/sub stances.

It is further envisaged that the fecal matter according to the disclosure is comprised in a composition, preferably a pharmaceutical composition, more preferably a liquid or solid dosage form, most preferably a capsule, a tablet, or a powder.

For oral administration, the fecal matter, e.g., one or more constituents of autologous feces, may be administered in solid dosage forms, such as capsules, tablets, and powders, or in liquid dosage forms, such as elixirs, syrups, and suspensions. Also a carrier can be applied, such as activated carbon.

The fecal matter may be used as medicament and/or accompanied by a physiologically acceptable carrier, which may be any inert carrier. For instance, non-limiting examples of suitable physiologically or pharmaceutically acceptable carriers include any well-known physiological or pharmaceutical carriers, buffers, diluents, and excipients. It will be appreciated that the choice for a suitable physiological carrier will depend upon the intended mode of administration of the composition as taught herein (e.g., oral) and the intended form of the composition (e.g., beverage, yogurt, powder, capsules, and the like). The skilled person knows how to select a physiologically acceptable carrier, which is suitable for or compatible with the compositions for use as taught herein.

It is particularly preferred that the fecal matter is comprised in and/or encapsulated by an (enteric) coating, preferably wherein the coating does not dissolve and/or disintegrate in the gastric environment of the subject. Such a coating may help the fecal matter reach the intended site for delivery, e.g., the duodenum, without suffering breakdown due to the acidic environment of the stomach. Preferred (enteric) coatings work by presenting a surface that is stable at the highly acidic pH found in the stomach, but break down more rapidly at a lower pH. For example, it will not dissolve in the gastric acids of the stomach (pH~3), but it will dissolve in the alkaline (pH 7-9) environment present in the small intestine or duodenum.

In an embodiment, the fecal matter according to the present disclosure may further comprise a mucosal binding agent. The term "mucosal binding agent" or "mucosal binding polypeptide" as used herein refers to an agent or a polypeptide that is capable of attaching itself to the gut mucosal surfaces of the gut mucosal barrier of a mammal (e.g., human). A variety of mucosal binding polypeptides have been disclosed in the art. Non-limiting examples of mucosal binding polypeptide include bacterial toxin membrane binding subunits including such as the B subunit of cholera toxin, the B subunit of the E. coli heat-labile enterotoxin, Bordetella pertussis toxin subunits S2, S3, S4 and/or S5, the B fragment of Diphtheria toxin and the membrane binding subunits of Shiga toxin or Shiga-like toxins. Other suitable mucosal binding polypeptides include bacterial fimbriae proteins such as including E. coli fimbriae K88, K99, 987P, F41, FAIL, CFAIII ICES1, CS2 and/or CS3, CFAIIV ICS4, CS5 and/or CS6), P fimbriae, or the like. Other non-limiting examples of fimbriae include Bordetella pertussis filamentous hemagglutinin, Vibrio cholerae toxin-coregulate pilus (TCP), Mannose-sensitive hemagglutinin (MSHA), fucose-sensitive hemagglutinin (PSHA), and the like. Still other mucosal-binding agents include viral attachment proteins including influenza and sendai virus hemagglutinins and animal lectins or lectin-like molecules including immunoglobulin molecules or fragments thereof, calcium-dependent (C-type) lectins, selectins, collectins or helix pomatis hemagglutinin, plant lectins with mucosabinding subunits include concanavalin A, wheat-germ agglutinin, phytohemagglutinin, abrin, ricin and the like.

In an embodiment, the composition for use as taught herein may be in liquid form, e.g., a stabilized suspension of fecal matter, e.g., comprising one or more constituents of autologous feces, in solid form, e.g., a powder of lyophilized constituents as taught herein. For example, a cryoprotectant such as lactose, trehalose or glycogen may be employed.

Optionally, the fecal matter may be encapsulated in capsules such as gelatin capsules, possibly together with inactive ingredients and powder carriers, such as e.g., glucose, lactose, sucrose, mannitol, starch, cellulose or cellulose derivatives, magnesium stearate, stearic acid, sodium saccharin, talcum, magnesium carbonate and the like.

In an embodiment, the fecal matter according to the disclosure may comprise one or more ingredients, which are suitable for promoting survival and/or viability and/or maintaining the and/or integrity of the fecal matter or constituents thereof e.g., during storage and/or during exposure to bile and/or during passage through the gastrointestinal tract of a mammal (e.g., a human). Non-limiting examples of such ingredients include an enteric coating as described herein before, and/or controlled release agents allowing passage through the stomach. The skilled person knows how to select suitable ingredients for ensuring that the fecal matter reaches its intended destination, where it exerts its action.

In an embodiment, the compositions for use as taught herein may further comprise ingredients selected from the group consisting of prebiotics, probiotics, carbohydrates, polypeptides, lipids, vitamins, minerals, medicinal agents, preservative agents, antibiotics, or any combination thereof.

In a particularly preferred embodiment, the fecal matter according to the present disclosure is combined with bacteria from the genus *Eubacterium, Intestinimonas, Bifidobacteria, Lactobacillales* and/or *Akkermansia*, preferably chosen from the group consisting of *Bifidobacterium animalis* sub *lactis* or *Bifidobacterium breve, Lactobacillus plantarum. Lactobacillus rhamnosus, Lactobacillus acidophilus, Eubacterium hallii, Intestinimonas butyriciproducens,* and/or *Akkermansia muciniphila*. A total of between $10^4$ and $10^{14}$, $10^6$ and $10^{12}$, preferably between $10^8$ and $10^{10}$, of such bacterial cells may preferably be used. The above-mentioned combination may provide for synergistic effects. The fecal matter and the bacteria may be comprised in different compositions, or together within a single composition (such as in a capsule or other dosage form as described herein).

The fecal matter according to the disclosure may additionally or alternatively be combined with hormone suppletion (thyroid, hydrocortisone, insulin etc), tumor necrosis factor alpha (TNFα) inhibitor, and/or DMARDs (rheumatoid arthritis) preferably chosen from the group consisting of infliximab, adalimumab, certolizumab pegol, and golimumab. The present inventors consider that treatment with a TNFα inhibitor may increase the response to treatment with fecal matter according to the present disclosure, and/or vice versa that treatment with fecal matter according to the present disclosure may increase the response to treatment with a TNFα inhibitor. Preferably, the TNFα inhibitor is administered in a different or the same composition as the fecal matter (such as in a capsule or other dosage form as described herein). The TNFα inhibitor may be administered at least (or at most) 1, 2, 3, 4 times weekly or daily and/or intravenously/orally in a dose of, for example, 1-10, 2-8, 3-7, 4-6, or 5 mg/kg.

It is further envisaged that the fecal matter for use according to the disclosure is present in lyophilized and/or microencapsulated form, e.g., a capsule comprising the. Preferably, the fecal matter is present in solid, lyophilized or dried form (i.e., containing less than 20, 10, 5, 2, 1, wt. % water), for example, in powder or granular form. For example, it may be present in microencapsulated form. The skilled person is capable of lyophilizing or microencapsulating the fecal matter based on well-known techniques, wherein oxygen-free conditions may be applied to preserve viability of any bacteria contained in the fecal matter.

The technique of microencapsulation is well-known in the art for preserving bacteria (e.g., as reviewed by Serna-Cock and Vallejo-Castillo, 2013. *Afr J of Microbiol Res,* 7(40): 4743-4753). For example, any of the preservation techniques and preservation systems taught by Serna-Cock and Vallejo-Castillo may be employed in the present disclosure.

Lyophilisation methods include, without limitation, slow, gradual freezing to −40° C. before drying, rapid freezing by placing at −80° C. before drying, or ultra rapid freezing by dripping cells with cryoprotectant in liquid nitrogen before drying. Cryoprotectants are often employed to protect compositions during lyophilisation and to enhance shelf-life. Without limitation, a cryoprotectant selected from the group consisting of sucrose, maltose, maltodextrin, trehalose, mannitol, sorbitol, inulin, glycerol, DMSO, ethylene glycol, propylene glycol, 2-methyl-2,4-pentanediol, polyethylene glycol, polyvinylpyrrolidone, polyvinyl alcohol, polyglycerol, skim milk powder, milk protein, whey protein, UHT milk, betaine, adonitol, sucrose, glucose, lactose or any combination thereof, may be employed.

Prebiotics such as starch and wheat bran may further be added to the fecal matter of the present disclosure, e.g., before lyophilisation to enhance the efficacy thereof. Addition of antioxidants such as riboflavin, riboflavin phosphate or a physiologically acceptable salt thereof, glutathione, ascorbate, glutathion and cysteine to the lyophilisation mixture may further enhance the viability of any bacteria contained in the fecal matter according to the present disclosure.

The fecal matter can be stored for long time (e.g., at least 10, 20, 40 52 weeks or at least 1, 2, 3 years) after addition of a cryoprotectant as disclosed herein, for example, glycerol and/or freezing at −80° C. In addition, or alternatively, freeze drying stabilizes the fecal matter over such period. Finally, one may also inoculate the fecal matter as described by de Vos (2013 *Microb Biotechnol.* 2013 July; 6(4):316-25).

In an embodiment, the fecal matter for use as taught herein may be, or may be comprised in, a food or food supplement composition. Such food or food supplement composition may include a dairy product, more preferably a fermented dairy product, preferably a yogurt or a yogurt drink.

In an embodiment, the compositions for use as taught herein may further comprise one or more ingredients, which further enhance the nutritional value and/or the therapeutic value of the fecal matter as taught herein. For instance, it may be advantageous to add one or more ingredients (e.g., nutritional ingredients, veterinary or medicinal agents etc.) selected from proteins, amino acids, enzymes, mineral salts, vitamins (e.g., thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g., water-soluble and water-insoluble monosaccharides, disaccharides, and polysaccharides), medicinal compounds (e.g., antibiotics), antioxidants, trace element ingredients (e.g., compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value.

In the context of this disclosure, the subject receiving the treatment is preferably an animal, more preferably a mammal, most preferably a human. As will be clear, the present treatment is preferably not performed as control or placebo treatment and/or within a clinical trial, i.e., a study in which participants are assigned to groups that either receive one or more intervention/treatment, one or more control or placebo intervention/treatment, or no intervention, so that researchers can evaluate the effects of the interventions on biomedical or health-related outcomes.

Further, in the context of this disclosure, it is not ruled out that the fecal matter can be fecal matter of a subject having the same disease as the subject to be treated, instead of fecal matter, which is autologous to the subject. In this regard, the fecal matter can be obtained from any subject having the same disease as the subject to be treated and administered, optionally after processing, to the subject to be treated (which may be the same subject). In this embodiment, all other (preferred/optional) technical features as described herein can be applied.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

Example 1

Administration of autologous fecal matter in different autoimmune conditions, and in comparison to administration of allogenic fecal matter Patients with conditions as indicated below are treated with infusion of either allogenic or autologous fecal matter by duodenal tube administration after bowel lavage (as in Example 3), according to the following 3 treatment arms:
1. multiple allogenic healthy donor fecal infusions at 0, 8 and 16 weeks.
2. multiple autologous (own) feces infusions at 0, 8 and 16 weeks.
3. multiple autologous (own) feces infusions combined with intravenous anti-TNFα (infliximab, 5 mg/kg) at 0, 8 and 16 weeks.

| No. of patients | Condition | Effect treatment 1 (patient 1) | Effect treatment 2 (patient 2) | Effect treatment 3 (patient 3) |
|---|---|---|---|---|
| 2 | Type 1 Diabetes | No effect | residual beta cell reserve is stabilized/improved over time (see also Examples 2 and 3), beneficial changes in T and B cell function | — |
| 2 | Hashimoto's disease | No effect | Slowed down progression of disease, less need of exogenous hormone supplementation, beneficial changes in T and B cell function, less perceived fatigability | — |
| 2 | Graves' disease | No effect | Slowed down progression of the disease, reduced enlargement of thyroid gland, less risk of remission and radioactive iodine treatment need, beneficial changes in T and B cell function | — |
| 2 | Addison's disease | No effect | Slowed down progression of disease, less need of exogenous hormone supplementation, beneficial changes in T and B cell function, reduced hyperpigmentation | — |
| 3 | Psoriasis | No effect | Slowed down progression of disease, somewhat reduced red inflamed areas, beneficial changes in T and B cell function | No apparent progression of disease, reduced red inflamed areas |
| 2 | Vitiligo | No effect | Slowed down progression of disease, some white patches on the skin disappear, beneficial changes in T and B cell function | — |
| 3 | Rheumatoid arthritis | No effect | Reduced progression of disease symptoms, and less pain around joints, less need of exogenous medication including DMARDS, beneficial changes in T and B cell function | No apparent progression of disease, some thickened joints return normal |
| 3 | Bechterew's disease | No effect | Slowed down progression of disease, less perceived lower back pain, less need of exogenous medication including DMARDS, beneficial changes in T and B cell function | No apparent progression of disease, less neck and lower back pain |
| 2 | Celiac disease | Ingestion of small amount of gluten leads to upset stomach, stomach pain, inflammation, diarrhea, gas | Ingestion of small amount of gluten leads to somewhat upset stomach but no pain, less diarrhea, less gas, less osteoporosis, beneficial changes in T and B cell function | — |
| 2 | Asthma | No effect | Slowed down disease progression, less episodes of coughing, shortness of breath (improved reversibility of FEV1 upon bronchodilators), less need of exogenous medication including synergy with bronchodilators, beneficial changes in T and B cell function | |

Similar results may be obtained if the autologous feces infusions are replaced by allogenic feces infusions obtained from subject(s) having the same disease as the subject to be treated. Further, it is expected that results similar to the putative effects as shown in the table above can be obtained with larger patient cohorts.

Example 2

Effect of Fecal Material Infusion on Residual Beta Cell Function in Patients with Diabetes Mellitus Type 1

1. Summary

Objective of Example: To investigate whether fecal material transplantation from either allogenic (healthy) or autologous (own) donor, administered through a small intestinal tube, has beneficial effects on immune status, betacell function (c-peptide release upon a mixed meal test (MMT) in recently diagnosed type 1 diabetes mellitus.

Study design: Double blind randomized controlled single center trial.

Study Population: Newly diagnosed (within 4-6 weeks of diagnosis) patients with type 1 diabetes (aged 18-30 years, BMI 18-25 kg/m$^2$, male/females, no concomitant medication use except insulin, plasma C-peptide >0.2 mmol/l and/or >1.2 ng/mL after MMT), fasting glucose 10-13 mmol/l and positive anti-GAD and/or anti-IA-2 titer concentrations. Moreover, healthy donors (n=17 male/female, BMI 18-25 kg/m2, no medication use, no family history of autoimmune diseases including type 1 diabetes mellitus and matched for EBV/CMV immune-status) were recruited.

Treatment: After bowel lavage with macrogol, patients were treated by three intestinal infusions via a duodenal tube of a solution derived from an allogenic (healthy donor) or autologous (own) feces.

Outcome measures: The primary endpoint is long term preservation in beta cell insulin secretion capacity stimulated C-peptide $AUC_{0-120}$ min response upon mixed-meal tolerance test (at 0, 2, 6, 9 and 12 months).

Sample Size: 10 subjects per group for this phase 1-2 trial. Patients were randomly assigned to allogenic or autologous fecal transplantation groups at a 1:1 ratio, thus 20 de novo type 1 diabetes in total. A planned interim analysis was performed when approximately 50% of all subjects were enrolled.

2. Objective

To investigate the effect of repetitive healthy donor feces infusion (allogenic) in comparison to own feces (autologous feces) on preservation of residual beta cell insulin secretion capacity: maximal C-peptide response (residual beta cell function) as assessed by MMT $AUC_{0-120\ min}$ at 0, 2, 6, 9 and 12 months.

3. Study Design

This was a double blind randomized controlled single center trial. Patients were randomized to the following 2 treatments in a 1:1 fashion:

1. multiple allogenic healthy donor fecal infusions at 0, 8 and 16 weeks.

2. multiple autologous (own) feces infusions at 0, 8 and 16 weeks.

4. Study Population 4.1 Population (Base)

DM1 Recipients Inclusion Criteria

Newly diagnosed (<4-6 weeks of diagnosis) patients with type 1 diabetes (aged 18-30 years, BMI 18-25 kg/m2, with still residual beta cell function (as indicated by plasma C peptide >0.2 mmol/l and/or >1.2 ng/mL after MMT), male/females, were recruited. DM1 Recipients exclusion criteria Subjects with diagnosis or symptoms of other autoimmune disease (eg hypo- or hyperthyroidism, coeliakie, rheumatoid arthritis or inflammatory bowel disease like Crohn/colitis ulcerosa) did not participate. Also, antibiotics use in the last 3 months and antiacids or PPI use was an exclusion criterion.

Donors

Healthy male/female volunteers, aged 18-30 years, BMI 18-25 kg/m2, no medication use, no family history of autoimmune diseases including type 1 diabetes mellitus and matched for EBV/CMV immune status were recruited as donors. Of note, Dm1 patients received 3 fecal transplantations from the same donor.

4.1 Inclusion Criteria

No concomitant medication use except insulin, peak stimulated C-peptide level >0.4 pmol/mL (and/or >1.2 ng/mL following an MMT), positive antiGAD/anti-IA-2 titers and a fasting glucose between 10-13 mmol/1.

4.2 Exclusion Criteria

Use of concomitant medication including proton pomp inhibitor (PPI) and antibiotics past three months, smoking, (expected) prolonged compromised immunity (due to recent cytotoxic chemotherapy or HIV infection with a CD4 count <240).

5. Treatment of Subjects 5.1 Protocol Fecal Transplantation

Patients were treated with infusion of allogenic or autologous feces by duodenal tube after bowel lavage. DM1 patients were randomized by sealed envelopes to the following 2 treatment arms:

1. multiple allogenic healthy donor fecal infusions at 0, 8 and 16 weeks.

2. multiple autologous (own) feces infusions at 0, 8 and 16 weeks.

5.1.1 Fecal Therapy (Weeks 0, 8 and 16 Weeks) Consists of:

1. Morning stool sample (100-200 gram) is collected by recipient & donor and brought to AMC for processing.

2. Meanwhile, gastro-duodenoscopy was performed for positioning of duodenal tube at baseline and 6 months (without tube). For fecal therapy, duodenal tube were positioned with CoreTrack magnetic device. Each duodenal tube positioned with CoreTrack was checked for correct anatomic position (to prevent infusion in stomach) by abdominal x-ray at baseline, 8 and 16 weeks, n=3 in total at 0.7 mSv per x-ray amounts to 2.1 mSv in 6 months (which equals the yearly average background radiation exposure).

3. Thereafter, bowel lavage with 2-3 liters of Clean Prep through the duodenal tube (according to standard protocols) was performed to ensure complete bowel lavage (duration 3-4 hours).

4. Finally, feces mixed in ~500 cc saline (filtered, <6 hours after processing) allogenic donor feces or autologous feces were infused in the duodenum through positioned duodenal tube.

6. Methods 6.1 Study Parameters 6.1.1 Effect on Residual Beta Cell Function Upon Multiple Allogenic Fecal Infusion Primary endpoint is change in residual beta cell function (stimulated C-peptide response upon mixed-meal tolerance $AUC_{0-120\ min}$) at 0, 2, 6, 9 and 12 months. A 2 hour (−10, 0, 15, 30, 45, 60, 90, 120 min) mixed meal test at 6 ml per kg body weight (max 360 ml per MMT of Boost™ Nutritional Drink, Nestle, Vevey, Switzerland: 33% carbohydrates, 57% fat and 15% protein) was performed as previously published (e.g., Herold et al *N Eng J Med* 2002; 346(22):1692-8;

Moran et al, Lancet. 2013 Jun. 1; 381(9881):1905-15). C-peptide was assayed from plasma at all of these time points with the Human C-Peptide Radioimmunoassay (Merck) with CV of 6.4%. An $AUC_{0-120\ min}$ (which is the area under the concentration (pmol/l) vs. time curve (AUC) between 0 and 120 minutes during mixed meal tolerance test (MMTT)) was determined. The AUC values were derived according to the trapezoidal rule. AUC mean 0-120 min denotes the $AUC_{0-120\ min}$ divided by the length of the time period (i.e., 120), and hence gives the mean level during the time period 0-120 minutes.

6.2 Randomisation, Blinding and Treatment Allocation

Patients were randomized by a computer. Blinding was guaranteed by collecting donor as well as recipient feces at the first fecal transplant (which is used as a placebo). On the day of fecal transplantation both patient and donors delivered faeces produced that morning. Randomisation and preparation of the feces was performed by one of the research assistants having no role in the further part of the study. Feces was put in a 500 ml glass bottle and looked like a brownish fluid not recognizable as feces from the donor or patient and subsequently given to the investigator who performed nasoduodenal tube infusion. Both patient, donor and investigator were blinded.

6.3 Study Procedures

In total DM1 subjects spent 34 hours (4 full study days) on this study divided over 9 visits in 12 months. The healthy donors spent 6 hours in total on this study during 1 year. Donor feces was collected from healthy (n=17, BMI 18-25 kg/m$^2$, male/female, non-smoking) subjects. Exclusion criteria for healthy donors were:

1. diarrhoea
2. family history of autoimmune diseases (type 1 diabetes, Hashimoto hypothyroidism, Graves hyperthyroidism, rheumatoid arthritis, inflammatory bowel diseases eg. Crohn's disease, Colitus ulcerosa or coeliakie)
3. HIV, HAV, HBV, HCV, active CMV, active EBV
4. Unsafe sex practice (questionnaire)
5. presence of fecal bacterial pathogens (*salmonella, Shigella, Campylobacter, Yersinia*) or parasites
6. positive *C. difficile* stool test
7. any medication use including PPI and antibiotics
8. smoking Individuals with an increased risk for one of the above conditions (homosexual contacts, recent blood transfusions) were excluded, and donors were not recruited amongst health care providers.

Preparation Fecal Clysma:

Donors delivered fresh feces sample (100-200 gram on average) at the day of infusion (produced within 6 hours before use). After collection in plastic flask, feces was covered by saline and stored at room temperature. Time of collection was written down. All procedures were performed at the department of Clinical Bacteriology, AMC Amsterdam. All steps were performed in fume-hood by an experienced lab co-worker. Fresh feces was covered with 500 ml sterile saline (0.9% NaCl) transferred to a blender and mixed for 10 minutes. The homogenized solution was then filtered twice through a clean metal sieve and food derived debris of too large size were removed. Hereafter, the homogenized solution was decanted through a clean metal funnel into a 1000 cc sterile glass bottle. Thereafter, a sample of the processed fecal infusate was taken for later analysis and the bottle was kept on normal room temperature (17° C.) until the patients was finished with bowel lavage.

7. Results

The results are shown in FIG. 1, where residual beta cell reserve (AUC mixed meal test stimulated C-peptide response) is depicted on the Y-axis, and time in months on the X-axis. The lower, straight line represents the normal decay in residual beta cell reserve over time in Diabetes mellitus Type 1 (DM1) patients (without treatment). The dashed line with the filled dots represents residual beta cell reserve over time in DM1 patients who received fecal material from healthy donors. The continuous line with open dots represents residual beta cell reserve over time in DM1 patients who received autologous (own) fecal material. Surprisingly, residual beta cell reserve was stabilized/improved over time in DM1 patients who received autologous (own) fecal material in their duodenum. FIG. 1 also shows that decay of residual beta cell reserve is somewhat slowed down in DM1 patients who received fecal material from healthy donors in their duodenum.

Example 3

Exogenous Insulin Use (E/Kg Bodyweight) and HbA1c are Reduced in Type 1 Diabetes Patients Upon Administration of Autologous Fecal Matter It was found in different clinical phenotypes that Glycated HB can be significantly decreased upon administration of autologous fecal matter. See FIG. 2. The reduced exogenous insulin needs suggests there is remaining endogenous (own) insulin production, thereby showing potential to extend the honeymoon period in Type 1 Diabetes mellitus.

Figure 2:
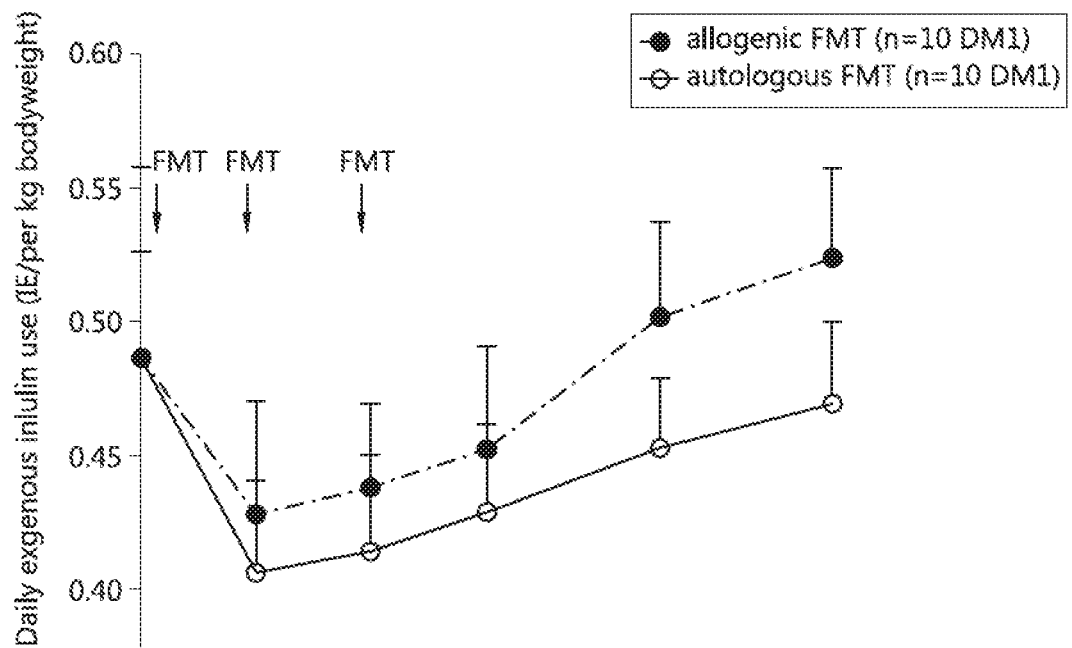
FIG. 2: The upper graph of FIG. 2 shows the exogenous need of insulin in type 1 Diabetes patients who received autologous fecal matter in comparison to type 1 Diabetes patients who received fecal matter from a donor; the lower graph of FIG. 2 shows the level of glycated Hemoglobin HbA1c over time in type 1 Diabetes patients who received autologous fecal matter in comparison to type 1 Diabetes patients who received fecal matter from a donor. The continuous line with open dots represents, respectively, the effect on the need of exogenous insulin and on glycated Hemoglobin HbA1c over time in DM1 patients who received autologous (own) fecal material.
Figure 2:
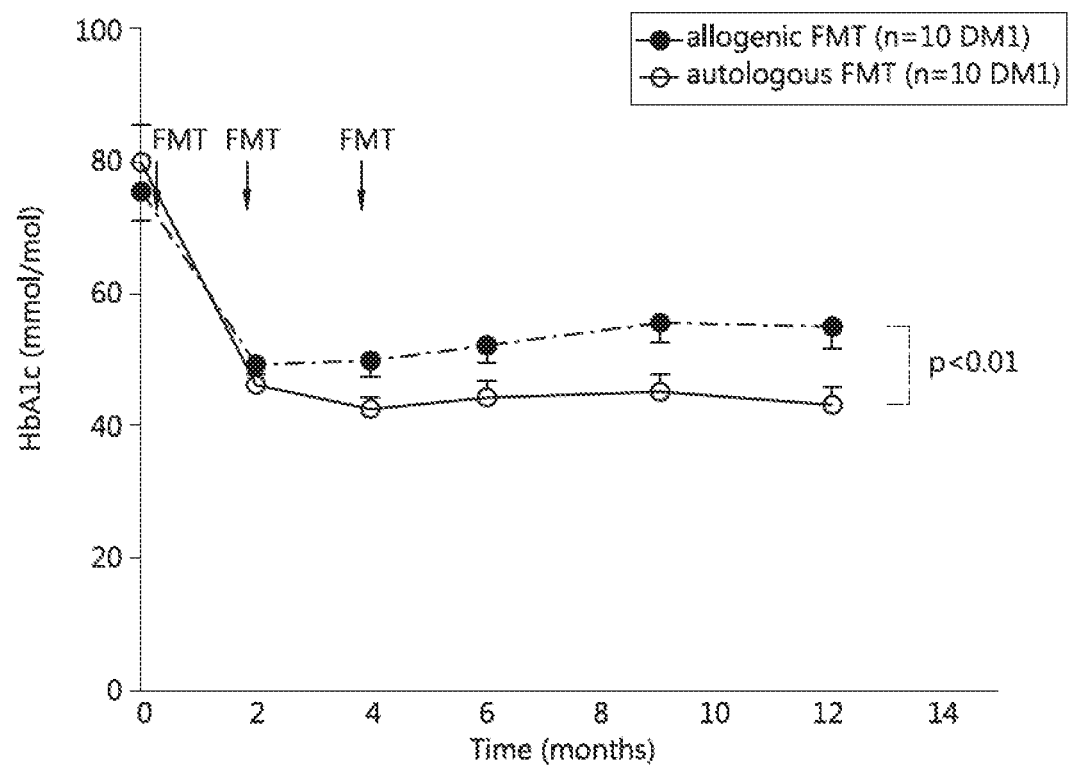

The upper graph of FIG. 2 reflects the exogenous need of insulin—based on insulin injections administered by/to the patients. This graph demonstrates the initial drop in insulin need as is usual in the so-called honeymoon period. Subsequently the need for exogenous insulin increases.

The need for exogenous insulin is lower in the group receiving autologous fecal matter compared to the group receiving fecal matter from a donor. This correlates with the better preservation of beta cell function in the autologous group (shown herein before).

The lower graph of FIG. 2 shows the level of glycated Hemoglobin HbA1c over time HbA1c reflects the level of glycemic control in the past period (6-8 weeks); the lower, the better. Notably, the HbA1c level in the group receiving autologous fecal matter is lower compared to the group receiving fecal matter from a donor. This is another confirmation of the maintenance of beta cell function in the autologous group.

It is important to emphasize that the glycemic control (reflected by HbA1c) is better in the group receiving autologous fecal matter (compared to the donor group) even though the amount of exogenous insulin used by the autologous group was less than the amounts used in the donor group.

The invention claimed is:

1. A method of treating an autoimmune disease in a subject, the method comprising:
    administration to the subject of feces that is autologous to the subject,
    wherein the autoimmune disease is type 1 diabetes mellitus, Hashimoto's disease, Graves' disease, Addison's disease, psoriasis, vitiligo, rheumatoid arthritis, Bechterew's disease, celiac disease, or asthma, and
    wherein the feces is obtained from the subject while having the autoimmune disease.

2. The method according to claim 1, wherein the autoimmune disease is selected from the group consisting of Type 1 Diabetes mellitus, psoriasis, vitiligo, rheumatoid arthritis, celiac disease, asthma, and Addison's disease.

3. The method according to claim 2, wherein the autoimmune disease is Hashimoto's disease, or Graves' disease.

4. The method according to claim 2, wherein the autoimmune disease is rheumatoid arthritis or Bechterew's disease.

5. The method according to claim 2, wherein the autoimmune disease is psoriasis.

6. The method according to claim 1, wherein the feces is administered to the small intestine of the subject.

7. The method according to claim 1, wherein the feces is comprised in liquid medium and/or does not comprise solids having a diameter of more than 1000 µm.

8. The method according to claim 1, wherein the feces is combined with a tumor necrosis factor alpha (TNFα) inhibitor.

9. The method according to claim 1, wherein the feces is combined with bacteria from the genus *Eubacterium, Intestinimonas, Bifidobacteria, Lactobacillales* and/or *Akkermansia*.

10. The method according to claim 1, wherein the feces is comprised in a composition.

11. The method according to claim 1, wherein the feces is comprised in and/or encapsulated by an enteric coating.

12. The method according to claim 1, wherein the feces is present in lyophilized and/or microencapsulated form.

13. The method according to claim 6, wherein the method comprises administering feces obtained from the subject to the duodenum of the subject.

14. The method according to claim 1, wherein the method comprises at least 2, 3, 4, 5, 6, 7, 8, 9, or 10 separate administrations of feces obtained from the subject to the small intestine to the subject.

15. The method according to claim 1, wherein the feces is administered by enteral, oral, nasal, or rectal administration, and/or by nasoduodenal tube administration.

16. The method according to claim 1, wherein the subject is a mammal.

17. The method according to claim 7, wherein the feces is obtained by mixing autologous feces with an aqueous medium and subsequent filtering and/or centrifugation of the mixture.

18. The method according to claim 9, wherein the bacteria is selected from the group consisting of *Bifidobacterium animalis* sub *lactis* or *Bifidobacterium breve, Lactobacillus plantarum, Lactobacillus rhamnosus, Lactobacillus acidophilus, Eubacterium hallii, Intestinimonas butyriciproducens,* and *Akkermansia muciniphila*.

19. The method according to claim 10, wherein the composition is a pharmaceutical composition selected from the group consisting of a liquid dosage form, a solid dosage form, a capsule, a tablet, and a powder.

20. The method according to claim 11, wherein the enteric coating does not dissolve and/or disintegrate in the gastric environment of the subject.

21. The method according to claim 14, wherein the separate administrations of feces are at intervals of at least 1 week between the separate administrations.

22. A method of treating a subject diagnosed as having an autoimmune disease, the method comprising:
administering feces autologous to the subject,
wherein the autoimmune disease is type 1 diabetes mellitus, Hashimoto's disease, Graves' disease, Addison's disease, psoriasis, vitiligo, rheumatoid arthritis, Bechterew's disease, celiac disease, or asthma,
wherein the administration of autologous feces is to the subject's small intestine, and
wherein the feces has been obtained from the subject while having the autoimmune disease.

23. A method of treating a subject for an autoimmune disease selected from the group consisting of type 1 diabetes, Hashimoto's disease, Graves' disease, Addison's disease, psoriasis, vitiligo, rheumatoid arthritis, Bechterew's disease, celiac disease, and asthma, the method comprising:
administering to the subject feces that is autologous to the subject,
wherein the feces is obtained from the subject while having the autoimmune disease,
wherein the feces is obtained by mixing autologous feces with an aqueous medium and subsequent filtering and/or centrifugation of the mixture, and
wherein the feces is comprised in liquid medium and/or does not comprise solids having a diameter of more than 1000 µm.

* * * * *